ulose phosphate isomerase activity was found in the extract of cells harvoring pT-HPIS-1. Thus, gene, which coded for hexulose phosphate isomerase, was obtained together with ORF which coded for hexulose phosphate synthase.

US006331428B1

(12) United States Patent
Kato

(10) Patent No.: US 6,331,428 B1
(45) Date of Patent: Dec. 18, 2001

(54) HEXULOSE PHOSPHATE ISOMERASE GENE

(75) Inventor: Nobuo Kato, Kameoka (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/185,501

(22) Filed: Nov. 4, 1998

Related U.S. Application Data

(63) Continuation-in-part of application No. 09/033,647, filed on Mar. 3, 1998, now abandoned.

(30) Foreign Application Priority Data

Jul. 9, 1997 (JP) .................................................. 10-194808
Aug. 28, 1997 (JP) .................................................. 9-233131

(51) Int. Cl.$^7$ ............................... C12N 9/90; C12N 1/20; C12N 15/63; C12N 5/00; C07H 21/04
(52) U.S. Cl. ........................ 435/233; 435/320.1; 435/325; 435/252.3; 536/23.1; 536/23.2
(58) Field of Search ................................ 435/233, 320.1, 435/325, 252.3; 536/23.1, 23.2

(56) References Cited

PUBLICATIONS

Hideshi Yanase et al., "Enzymatic preparation of [1–$^{13}$C] D–fructose–6–phosphate from [$^{13}$C] formaldehyde and D–ribose–5–phosphate*Methylomonas aminofaciens* 77 a", Appl. Microbiol Biotechnol. (1992) 37:301–304.

*Primary Examiner*—Charles L. Patterson, Jr.
*Assistant Examiner*—Peter P. Tung
(74) *Attorney, Agent, or Firm*—Oblon, Spivak, McClelland, Maier & Neustadt, P.C.

(57) ABSTRACT

Hexulose phosphate synthase was purified from *Mycobacterium gastri* to determine an amino acid sequence of the enzyme. Oligonucleotide primers to be used for PCR were synthesized on the basis of obtained amino acid sequence information. A DNA fragment, which was amplified by performing PCR by using a template of genomic DNA prepared from *Mycobacterium gastri*, was used as a probe so that colony hybridization was carried out with respect to a library comprising fragments obtained by digesting *Mycobacterium gastri* genomic DNA with PstI to obtain a positive clone. Thus, the DNA fragment which contains ORF encoding hexulose phosphate synthase was obtained. Furthermore, the DNA fragment cloned contained other ORF(ORF-1). The expression system of ORF-1 was constructed (pT-HPIS-1), and it was introduced into *Escherichia coli* cell. After the induction of the expression of ORF-1, the hexulose phosphate isomerase activity was found in the extract of cells harvoring pT-HPIS-1. Thus, gene, which coded for hexulose phosphate isomerase, was obtained together with ORF which coded for hexulose phosphate synthase.

20 Claims, No Drawings

SEQUENCE LISTING

<160> NUMBER OF SEQ ID NOS: 19

<210> SEQ ID NO 1
<211> LENGTH: 30
<212> TYPE: PRT
<213> ORGANISM: Mycobacterium gastri

<400> SEQUENCE: 1

Met Lys Leu Gln Val Ala Ile Asp Leu Leu Ser Thr Glu Ala Ala Leu
1               5                   10                  15

Glu Leu Ala Gly Lys Val Ala Glu Tyr Val Asp Ile Ile Glu
            20                  25                  30

<210> SEQ ID NO 2
<211> LENGTH: 16
<212> TYPE: PRT
<213> ORGANISM: Mycobacterium gastri

<400> SEQUENCE: 2

Val Ala Glu Tyr Val Asp Ile Ile Glu Leu Gly Thr Pro Leu Ile Lys
1               5                   10                  15

<210> SEQ ID NO 3
<211> LENGTH: 7
<212> TYPE: PRT
<213> ORGANISM: Mycobacterium gastri

<400> SEQUENCE: 3

Ile Val Phe Ala Asp Met Lys
1               5

<210> SEQ ID NO 4
<211> LENGTH: 13
<212> TYPE: PRT
<213> ORGANISM: Mycobacterium gastri

<400> SEQUENCE: 4

Ala Thr Arg Ala Gln Glu Val Arg Ala Leu Gly Ala Lys
1               5                   10

<210> SEQ ID NO 5
<211> LENGTH: 13
<212> TYPE: PRT
<213> ORGANISM: Mycobacterium gastri

<400> SEQUENCE: 5

Phe Val Glu Met His Ala Gly Leu Asp Glu Gln Ala Lys
1               5                   10

<210> SEQ ID NO 6
<211> LENGTH: 12
<212> TYPE: PRT
<213> ORGANISM: Mycobacterium gastri

<400> SEQUENCE: 6

Ala Arg Val Pro Phe Ser Val Ala Gly Gly Val Lys
1               5                   10

<210> SEQ ID NO 7
<211> LENGTH: 9
<212> TYPE: PRT
<213> ORGANISM: Mycobacterium gastri

```
<400> SEQUENCE: 7

Val Ala Thr Ile Pro Ala Val Gln Lys
1               5

<210> SEQ ID NO 8
<211> LENGTH: 23
<212> TYPE: DNA
<213> ORGANISM: Artificial Sequence
<220> FEATURE:
<221> NAME/KEY: misc_feature
<223> OTHER INFORMATION: Description of Artificial Sequence: synthentic
      DNA
<221> NAME/KEY: Unsure
<222> LOCATION: (9)..(9)
<223> OTHER INFORMATION: n=i
<221> NAME/KEY: Unsure
<222> LOCATION: (15)..(15)
<223> OTHER INFORMATION: n=a or g or t or c
<221> NAME/KEY: Unsure
<222> LOCATION: (18)..(18)
<223> OTHER INFORMATION: n=i

<400> SEQUENCE: 8
atgaarytnc argtngcnat hga                                          23

<210> SEQ ID NO 9
<211> LENGTH: 20
<212> TYPE: DNA
<213> ORGANISM: Artificial Sequence
<220> FEATURE:
<221> NAME/KEY: misc_feature
<223> OTHER INFORMATION: Description of Artificial Sequence:synthetic
      DNA
<221> NAME/KEY: Unsure
<222> LOCATION: (3)..(3)
<223> OTHER INFORMATION: n= a or g or t or c
<221> NAME/KEY: Unsure
<222> LOCATION: (15)..(15)
<223> OTHER INFORMATION: n= a or g or t or c

<400> SEQUENCE: 9
ccngcrtgca tytcnacraa                                              20

<210> SEQ ID NO 10
<211> LENGTH: 42
<212> TYPE: DNA
<213> ORGANISM: Artificial Sequence
<220> FEATURE:
<221> NAME/KEY: misc_feature
<223> OTHER INFORMATION: Description of Artificial Sequence:synthetic
      DNA

<400> SEQUENCE: 10
cgaaatcgat aaaaatgacg caagccgcag aagccgacgg cg                     42

<210> SEQ ID NO 11
<211> LENGTH: 30
<212> TYPE: DNA
<213> ORGANISM: Artificial Sequence
<220> FEATURE:
<221> NAME/KEY: misc_feature
<223> OTHER INFORMATION: Description of Artificial Sequence:synthetic
      DNA

<400> SEQUENCE: 11
aattccagct ctagacaagg cggtacggcg                                   30

<210> SEQ ID NO 12
<211> LENGTH: 2967
```

```
<212> TYPE: DNA
<213> ORGANISM: Mycobacterium gastri
<220> FEATURE:
<221> NAME/KEY: CDS
<222> LOCATION: (608)..(1204)
<221> NAME/KEY: CDS
<222> LOCATION: (1281)..(1901)
<221> NAME/KEY: CDS
<222> LOCATION: (2146)..(2967)

<400> SEQUENCE: 12
```

```
cgagctcgga aaccactccc gcatgatgtc ggtctcgggc tcgggctgat tgacgacgaa      60
ggttcccccg ctgcggccgc ggcgcgtctc gacgacccct cgttcgcgca gttccgacaa     120
cgcttcccgc agcgttgcgc cgccgacccc gaacatctcc gaaagcgcgg cctcaggggg     180
taggcgttca cctactttga gcagcccgag ggcgatcgcc ttggagattc tctcgacaat     240
cgcgtcggcc ctctcgattt ccggcaggga ccgataaatc tgcgactgga aggggtcgg     300 cgtggccaaa agtctgcgct ccgaaaatgg actacgaggt gagtcgatcc taggtcgaag     360
ccgtggcccg cggtgccgac tacgcgtcg cggttggggt tgctgacgcg cctcggcaca      420
tcaccgctgc gcacgctccg ccgggaccgt acggaggggg cagggtggct gaccaatcca     480
aaagtgtagt cagaaccgtc agaaaacagt attaccccca cccgttcgct tcgggattat     540
tggcttcagt caagccaatc atccgttcgg ccgtcacgg cccgacgacc gatcgaaggg     600 ggtaacc atg acg caa gcc gca gaa gcc gac ggc gcc gtg aag gtc gtc       649
        Met Thr Gln Ala Ala Glu Ala Asp Gly Ala Val Lys Val Val
        1               5                   10 gga gac gac atc acc aac aac ctt tcc ctt gtt cgg gac gag gtc gcg       697
Gly Asp Asp Ile Thr Asn Asn Leu Ser Leu Val Arg Asp Glu Val Ala
15                  20                  25                  30 gac acc gcg gcg aaa gtc gac ccg gag cag gtg gct gtc ctc gct cgc       745
Asp Thr Ala Ala Lys Val Asp Pro Glu Gln Val Ala Val Leu Ala Arg
                35                  40                  45 caa atc gtc cag cct gga cgg gtt ttc gtg gcg ggc gcc ggt cgc agc       793
Gln Ile Val Gln Pro Gly Arg Val Phe Val Ala Gly Ala Gly Arg Ser
            50                  55                  60 ggg ctc gtc ctg cgc atg gcc gcc atg cgg ctg atg cac ttc ggc ctc       841
Gly Leu Val Leu Arg Met Ala Ala Met Arg Leu Met His Phe Gly Leu
65                  70                  75 acc gtg cac gtc gcg ggc gac acc acc ccg gca atc tca gcc ggc           889
Thr Val His Val Ala Gly Asp Thr Thr Thr Pro Ala Ile Ser Ala Gly
    80                  85                  90 gat ctg ctg ctg gtg gct tcc ggc tcg ggc acc acc tcc ggt gtg gtc       937
Asp Leu Leu Leu Val Ala Ser Gly Ser Gly Thr Thr Ser Gly Val Val
95                  100                 105                 110 aag tcc gcc gag acg gcc aag aag gcc ggg gcg cgc atc gcc gcc ttc       985
Lys Ser Ala Glu Thr Ala Lys Lys Ala Gly Ala Arg Ile Ala Ala Phe
                115                 120                 125 acc acc aac ccg gat tct ccg ctg gcc ggt ctg gcc gac gcc gtg gtg      1033
Thr Thr Asn Pro Asp Ser Pro Leu Ala Gly Leu Ala Asp Ala Val Val
            130                 135                 140 atc atc ccc gcc gcg cag aag acc gat cac ggc tcg cac att tcg cgg      1081
Ile Ile Pro Ala Ala Gln Lys Thr Asp His Gly Ser His Ile Ser Arg
            145                 150                 155 cag tac gcc gga tcc ctt ttc gag cag gtg ctg ttc gtc gtc acc gaa      1129
Gln Tyr Ala Gly Ser Leu Phe Glu Gln Val Leu Phe Val Val Thr Glu
160                 165                 170 gcc gtg ttc cag tcg ctg tgg gat cac acc gag gtc gag gcc gag gaa      1177
Ala Val Phe Gln Ser Leu Trp Asp His Thr Glu Val Glu Ala Glu Glu
175                 180                 185                 190
```

```
ctc tgg acg cgc cac gcc aac ctc gag tgacccggac ctcgacgacc       1224
Leu Trp Thr Arg His Ala Asn Leu Glu
                195 aactcttact tcacattcca tacccatcgc agtacccaac agaaagaagg caccca atg  1283
                                                              Met
                                                              200 aag ctc caa gtc gcc atc gac ctg ctg tcc acc gaa gcc gcc ctc gag   1331
Lys Leu Gln Val Ala Ile Asp Leu Leu Ser Thr Glu Ala Ala Leu Glu
            205                 210                 215 ctg gcc ggc aag gtt gcc gag tac gtc gac atc atc gaa ctg ggc acc   1379
Leu Ala Gly Lys Val Ala Glu Tyr Val Asp Ile Ile Glu Leu Gly Thr
            220                 225                 230 ccc ctg atc gag gcc gag ggc ctg tcg gtc atc acc gcc gtc aag aag   1427
Pro Leu Ile Glu Ala Glu Gly Leu Ser Val Ile Thr Ala Val Lys Lys
        235                 240                 245 gct cac ccg gac aag atc gtc ttc gcc gac atg aag acc atg gac gcc   1475
Ala His Pro Asp Lys Ile Val Phe Ala Asp Met Lys Thr Met Asp Ala
        250                 255                 260 ggc gag ctc gaa gcc gac atc gcg ttc aag gcc ggc gct gac ctg gtc   1523
Gly Glu Leu Glu Ala Asp Ile Ala Phe Lys Ala Gly Ala Asp Leu Val
265                 270                 275                 280 acg gtc ctc ggc tcg gcc gac gac tcc acc atc gcg ggt gcc gtc aag   1571
Thr Val Leu Gly Ser Ala Asp Asp Ser Thr Ile Ala Gly Ala Val Lys
                285                 290                 295 gcc gcc cag gct cac aac aag ggc gtc gtc gtc gac ctg atc ggc atc   1619
Ala Ala Gln Ala His Asn Lys Gly Val Val Val Asp Leu Ile Gly Ile
            300                 305                 310 gag gac aag gcc acc cgt gca cag gaa gtt cgc gcc ctg ggt gcc aag   1667
Glu Asp Lys Ala Thr Arg Ala Gln Glu Val Arg Ala Leu Gly Ala Lys
        315                 320                 325 ttc gtc gag atg cac gct ggt ctg gac gag cag gcc aag ccc ggc ttc   1715
Phe Val Glu Met His Ala Gly Leu Asp Glu Gln Ala Lys Pro Gly Phe
        330                 335                 340 gac ctg aac ggt ctg ctc gcc gcc ggc gag aag gct cgc gtt ccg ttc   1763
Asp Leu Asn Gly Leu Leu Ala Ala Gly Glu Lys Ala Arg Val Pro Phe
345                 350                 355                 360 tcc gtg gcc ggt ggc gtg aaa gtt gcg acc atc ccc gca gtc cag aag   1811
Ser Val Ala Gly Gly Val Lys Val Ala Thr Ile Pro Ala Val Gln Lys
                365                 370                 375 gcc ggc gca gaa gtt gcc gtc gcc ggt ggc gcc atc tac ggt gca gcc   1859
Ala Gly Ala Glu Val Ala Val Ala Gly Gly Ala Ile Tyr Gly Ala Ala
            380                 385                 390 gac ccg gcc gcc gcc gcg aag gaa ctg cgc gcc gcg atc gcc            1901
Asp Pro Ala Ala Ala Ala Lys Glu Leu Arg Ala Ala Ile Ala
        395                 400                 405 tgatcctgat cgtttagcac tcccataacg gtggcgtccc gcatcctgaa agcagttgcg  1961
ggacgcaacc gtttggtttt tctaccctga aatagcgcat gagctcgccg ggcgcggtac  2021
tcgtctggag gcgtgtgtcg ctcggcggcg cgctccttcc tgggaagatc ccgcccgctg  2081
acactttcac gcaaccgtga ggtcgacgac gccgtaccgc cttgtcgaga gctggaattc  2141 cacc atg tcc gct gac cac ggt gat tcg agt gtg agg ccc gga cgc aac   2190
     Met Ser Ala Asp His Gly Asp Ser Ser Val Arg Pro Gly Arg Asn
                     410                 415                 420 ctg ctc cgg gat ccg cgc gat cgt cgc ttg aac cgc atc gcc ggt ccg   2238
Leu Leu Arg Asp Pro Arg Asp Arg Arg Leu Asn Arg Ile Ala Gly Pro
            425                 430                 435 tcc tcc ctt gtc ctg ttc gga gtc acg ggc gat ctc gcc cgg aag aaa   2286
Ser Ser Leu Val Leu Phe Gly Val Thr Gly Asp Leu Ala Arg Lys Lys
```

```
                440                 445                 450
ctc gtg ccc gcg gtg tac gac ctc gcc aac cgg ggt ctg ttg ccg ccg      2334
Leu Val Pro Ala Val Tyr Asp Leu Ala Asn Arg Gly Leu Leu Pro Pro
        455                 460                 465 agc ttt gcc ttg gtg ggc ttc ggc cgg cgc gaa tgg acg aac gag gac      2382
Ser Phe Ala Leu Val Gly Phe Gly Arg Arg Glu Trp Thr Asn Glu Asp
470                 475                 480                 485 ttc gcc gcc gag gtc aag gcg aac gtg aag gct tac gcc cga aca cct      2430
Phe Ala Ala Glu Val Lys Ala Asn Val Lys Ala Tyr Ala Arg Thr Pro
                490                 495                 500 ttc gac gag gcc gtg tgg gag caa ctc tcc gag ggc atc cgc ttc gtc      2478
Phe Asp Glu Ala Val Trp Glu Gln Leu Ser Glu Gly Ile Arg Phe Val
            505                 510                 515 caa ggc gcg ttc gac gac gag acg gcg ttc aaa cgg ctg cgc gcc acg      2526
Gln Gly Ala Phe Asp Asp Glu Thr Ala Phe Lys Arg Leu Arg Ala Thr
        520                 525                 530 ctg gag gat ctc gac gag cag cgc ggc acg cgc ggc aat tac gcc ttc      2574
Leu Glu Asp Leu Asp Glu Gln Arg Gly Thr Arg Gly Asn Tyr Ala Phe
    535                 540                 545 tac ctt tcg atc cca ccc aag gcc ttc gaa cag gtc tgc cgc cag ctc      2622
Tyr Leu Ser Ile Pro Pro Lys Ala Phe Glu Gln Val Cys Arg Gln Leu
550                 555                 560                 565 tcc gaa tcc ggg ctg gcg cag gcc gag aac gac aag tgg cgc cgg gtg      2670
Ser Glu Ser Gly Leu Ala Gln Ala Glu Asn Asp Lys Trp Arg Arg Val
                570                 575                 580 gtc atc gag aag ccg ttc gga cac gac ctc gag tcg gcc cgc caa ctc      2718
Val Ile Glu Lys Pro Phe Gly His Asp Leu Glu Ser Ala Arg Gln Leu
            585                 590                 595 aac gac gtc gtc gag tcc gtg ttc ccg ccg gac gcc gtg ttc cgg atc      2766
Asn Asp Val Val Glu Ser Val Phe Pro Pro Asp Ala Val Phe Arg Ile
        600                 605                 610 gac cat tac ctg ggc aag gag acg gtc cag aac atc ctg gcc ctg cgc      2814
Asp His Tyr Leu Gly Lys Glu Thr Val Gln Asn Ile Leu Ala Leu Arg
    615                 620                 625 ttc gcg aac cag ctc ttc gag ccg ctg tgg aac gcg aat tac gtt gac      2862
Phe Ala Asn Gln Leu Phe Glu Pro Leu Trp Asn Ala Asn Tyr Val Asp
630                 635                 640                 645 cac gta cag atc acg atg gcc gaa tcc atc ggc acc ggc ggc cgg gca      2910
His Val Gln Ile Thr Met Ala Glu Ser Ile Gly Thr Gly Gly Arg Ala
                650                 655                 660 ggt tac tac gac ggt gtc ggc gcg gcc cgc gac gtc atc cag aac cac      2958
Gly Tyr Tyr Asp Gly Val Gly Ala Ala Arg Asp Val Ile Gln Asn His
            665                 670                 675 ctg ctg cag                                                           2967
Leu Leu Gln
        680

<210> SEQ ID NO 13
<211> LENGTH: 199
<212> TYPE: PRT
<213> ORGANISM: Mycobacterium gastri

<400> SEQUENCE: 13

Met Thr Gln Ala Ala Glu Ala Asp Gly Ala Val Lys Val Val Gly Asp
1               5                   10                  15

Asp Ile Thr Asn Asn Leu Ser Leu Val Arg Asp Glu Val Ala Asp Thr
            20                  25                  30

Ala Ala Lys Val Asp Pro Glu Gln Val Ala Val Leu Ala Arg Gln Ile
        35                  40                  45
```

```
Val Gln Pro Gly Arg Val Phe Val Ala Gly Ala Gly Arg Ser Gly Leu
    50                  55                  60

Val Leu Arg Met Ala Ala Met Arg Leu Met His Phe Gly Leu Thr Val
65                  70                  75                  80

His Val Ala Gly Asp Thr Thr Thr Pro Ala Ile Ser Ala Gly Asp Leu
                    85                  90                  95

Leu Leu Val Ala Ser Gly Ser Gly Thr Thr Ser Gly Val Val Lys Ser
                100                 105                 110

Ala Glu Thr Ala Lys Lys Ala Gly Ala Arg Ile Ala Ala Phe Thr Thr
                115                 120                 125

Asn Pro Asp Ser Pro Leu Ala Gly Leu Ala Asp Ala Val Ile Ile
                130                 135                 140

Pro Ala Ala Gln Lys Thr Asp His Gly Ser His Ile Ser Arg Gln Tyr
145                 150                 155                 160

Ala Gly Ser Leu Phe Glu Gln Val Leu Phe Val Val Thr Glu Ala Val
                165                 170                 175

Phe Gln Ser Leu Trp Asp His Thr Glu Val Glu Ala Glu Leu Trp
                180                 185                 190

Thr Arg His Ala Asn Leu Glu
        195

<210> SEQ ID NO 14
<211> LENGTH: 207
<212> TYPE: PRT
<213> ORGANISM: Mycobacterium gastri

<400> SEQUENCE: 14

Met Lys Leu Gln Val Ala Ile Asp Leu Leu Ser Thr Glu Ala Ala Leu
1               5                   10                  15

Glu Leu Ala Gly Lys Val Ala Glu Tyr Val Asp Ile Ile Glu Leu Gly
                20                  25                  30

Thr Pro Leu Ile Glu Ala Glu Gly Leu Ser Val Ile Thr Ala Val Lys
                35                  40                  45

Lys Ala His Pro Asp Lys Ile Val Phe Ala Asp Met Lys Thr Met Asp
        50                  55                  60

Ala Gly Glu Leu Glu Ala Asp Ile Ala Phe Lys Ala Gly Ala Asp Leu
65                  70                  75                  80

Val Thr Val Leu Gly Ser Ala Asp Ser Thr Ile Ala Gly Ala Val
                85                  90                  95

Lys Ala Ala Gln Ala His Asn Lys Gly Val Val Asp Leu Ile Gly
                100                 105                 110

Ile Glu Asp Lys Ala Thr Arg Ala Gln Glu Val Arg Ala Leu Gly Ala
        115                 120                 125

Lys Phe Val Glu Met His Ala Gly Leu Asp Glu Gln Ala Lys Pro Gly
        130                 135                 140

Phe Asp Leu Asn Gly Leu Leu Ala Ala Gly Glu Lys Ala Arg Val Pro
145                 150                 155                 160

Phe Ser Val Ala Gly Gly Val Lys Val Ala Thr Ile Pro Ala Val Gln
                165                 170                 175

Lys Ala Gly Ala Glu Val Ala Val Ala Gly Gly Ala Ile Tyr Gly Ala
                180                 185                 190

Ala Asp Pro Ala Ala Ala Lys Glu Leu Arg Ala Ala Ile Ala
        195                 200                 205

<210> SEQ ID NO 15
```

```
<211> LENGTH: 274
<212> TYPE: PRT
<213> ORGANISM: Mycobacterium gastri

<400> SEQUENCE: 15

Met Ser Ala Asp His Gly Asp Ser Ser Val Arg Pro Gly Arg Asn Leu
1               5                   10                  15

Leu Arg Asp Pro Arg Asp Arg Arg Leu Asn Arg Ile Ala Gly Pro Ser
            20                  25                  30

Ser Leu Val Leu Phe Gly Val Thr Gly Asp Leu Ala Arg Lys Lys Leu
        35                  40                  45

Val Pro Ala Val Tyr Asp Leu Ala Asn Arg Gly Leu Leu Pro Pro Ser
    50                  55                  60

Phe Ala Leu Val Gly Phe Gly Arg Arg Glu Trp Thr Asn Glu Asp Phe
65                  70                  75                  80

Ala Ala Glu Val Lys Ala Asn Val Lys Ala Tyr Ala Arg Thr Pro Phe
                85                  90                  95

Asp Glu Ala Val Trp Glu Gln Leu Ser Glu Gly Ile Arg Phe Val Gln
            100                 105                 110

Gly Ala Phe Asp Asp Glu Thr Ala Phe Lys Arg Leu Arg Ala Thr Leu
        115                 120                 125

Glu Asp Leu Asp Glu Gln Arg Gly Thr Arg Gly Asn Tyr Ala Phe Tyr
    130                 135                 140

Leu Ser Ile Pro Pro Lys Ala Phe Glu Gln Val Cys Arg Gln Leu Ser
145                 150                 155                 160

Glu Ser Gly Leu Ala Gln Ala Glu Asn Asp Lys Trp Arg Arg Val Val
                165                 170                 175

Ile Glu Lys Pro Phe Gly His Asp Leu Glu Ser Ala Arg Gln Leu Asn
            180                 185                 190

Asp Val Val Glu Ser Val Phe Pro Pro Asp Ala Val Phe Arg Ile Asp
        195                 200                 205

His Tyr Leu Gly Lys Glu Thr Val Gln Asn Ile Leu Ala Leu Arg Phe
    210                 215                 220

Ala Asn Gln Leu Phe Glu Pro Leu Trp Asn Ala Asn Tyr Val Asp His
225                 230                 235                 240

Val Gln Ile Thr Met Ala Glu Ser Ile Gly Thr Gly Arg Ala Gly
                245                 250                 255

Tyr Tyr Asp Gly Val Gly Ala Ala Arg Asp Val Ile Gly Asn His Leu
            260                 265                 270

Leu Gln

<210> SEQ ID NO 16
<211> LENGTH: 737
<212> TYPE: DNA
<213> ORGANISM: Bacillus subtilis
<220> FEATURE:
<221> NAME/KEY: CDS
<222> LOCATION: (113)..(667)

<400> SEQUENCE: 16
tgatccagca aaagcctgac cttgtcattg tcgggggcgg aattacaagc gcagctgata      60
aggcggaaac agcttcaaaa atgaagcagc tgattgtcca aggataactc cg atg aaa    118
                                                            Met Lys
                                                              1 acg act gaa tac gta gcg gaa att ctc aat gag tta cac aat tca gca    166
Thr Thr Glu Tyr Val Ala Glu Ile Leu Asn Glu Leu His Asn Ser Ala
          5                  10                  15
```

```
gct tat att tct aat gaa gaa gct gac cag ctt gcc gat cac att ctt         214
Ala Tyr Ile Ser Asn Glu Glu Ala Asp Gln Leu Ala Asp His Ile Leu
    20                  25                  30 tca tcc cac caa att ttc acc gcg ggt gcg ggg cgg tct ggc ctg atg         262
Ser Ser His Gln Ile Phe Thr Ala Gly Ala Gly Arg Ser Gly Leu Met
 35                  40                  45                  50 gca aaa tcc ttc gcg atg aga ctg atg cac atg ggc ttc aac gcc cat         310
Ala Lys Ser Phe Ala Met Arg Leu Met His Met Gly Phe Asn Ala His
                 55                  60                  65 ata gta ggt gag att ctc act ccg ccg ctc gcc gaa gga gat cta gtt         358
Ile Val Gly Glu Ile Leu Thr Pro Pro Leu Ala Glu Gly Asp Leu Val
                     70                  75                  80 att atc ggc tca gga tca ggc gag aca aag agc ttg att cat acc gca         406
Ile Ile Gly Ser Gly Ser Gly Glu Thr Lys Ser Leu Ile His Thr Ala
                 85                  90                  95 gca aaa gca aaa agc tta cac gga att gtt gcc gct tta acc atc aat         454
Ala Lys Ala Lys Ser Leu His Gly Ile Val Ala Ala Leu Thr Ile Asn
            100                 105                 110 ccg gaa tca agc atc gga aaa caa gcg gac ctc atc atc aga atg cct         502
Pro Glu Ser Ser Ile Gly Lys Gln Ala Asp Leu Ile Ile Arg Met Pro
115                 120                 125                 130 ggt tcc cct aaa gac cag tct aac gga agc tat aaa acc att cag cca         550
Gly Ser Pro Lys Asp Gln Ser Asn Gly Ser Tyr Lys Thr Ile Gln Pro
                135                 140                 145 atg gga tca tta ttt gaa caa act ttg ctg ctc ttc tat gat gca gtg         598
Met Gly Ser Leu Phe Glu Gln Thr Leu Leu Leu Phe Tyr Asp Ala Val
            150                 155                 160 att tta aaa ctc atg gag aaa aaa ggt ctc gat tct gaa act atg ttc         646
Ile Leu Lys Leu Met Glu Lys Lys Gly Leu Asp Ser Glu Thr Met Phe
        165                 170                 175 act cac cac gca aac ctt gaa tagcatcaca caaccggcct gaagatcagg            697
Thr His His Ala Asn Leu Glu
    180                 185 ccggttttat tttttctaaa ataaaactttt aaacccaaaa                            737
```

<210> SEQ ID NO 17
<211> LENGTH: 185
<212> TYPE: PRT
<213> ORGANISM: Bacillus subtilis

<400> SEQUENCE: 17

```
Met Lys Thr Thr Glu Tyr Val Ala Glu Ile Leu Asn Glu Leu His Asn
 1               5                  10                  15

Ser Ala Ala Tyr Ile Ser Asn Glu Glu Ala Asp Gln Leu Ala Asp His
                20                  25                  30

Ile Leu Ser Ser His Gln Ile Phe Thr Ala Gly Ala Gly Arg Ser Gly
            35                  40                  45

Leu Met Ala Lys Ser Phe Ala Met Arg Leu Met His Met Gly Phe Asn
 50                  55                  60

Ala His Ile Val Gly Glu Ile Leu Thr Pro Pro Leu Ala Glu Gly Asp
 65                  70                  75                  80

Leu Val Ile Ile Gly Ser Gly Ser Gly Glu Thr Lys Ser Leu Ile His
                85                  90                  95

Thr Ala Ala Lys Ala Lys Ser Leu His Gly Ile Val Ala Ala Leu Thr
            100                 105                 110

Ile Asn Pro Glu Ser Ser Ile Gly Lys Gln Ala Asp Leu Ile Ile Arg
        115                 120                 125
```

```
Met Pro Gly Ser Pro Lys Asp Gln Ser Asn Gly Ser Tyr Lys Thr Ile
    130                 135                 140

Gln Pro Met Gly Ser Leu Phe Glu Gln Thr Leu Leu Leu Phe Tyr Asp
145                 150                 155                 160

Ala Val Ile Leu Lys Leu Met Glu Lys Lys Gly Leu Asp Ser Glu Thr
                165                 170                 175

Met Phe Thr His His Ala Asn Leu Glu
                180                 185

<210> SEQ ID NO 18
<211> LENGTH: 40
<212> TYPE: DNA
<213> ORGANISM: Artificial Sequence
<220> FEATURE:
<221> NAME/KEY: misc_feature
<223> OTHER INFORMATION: Description of Artificial Sequence:synthetic
      DNA

<400> SEQUENCE: 18
aagcatcgat aaaatgaaaa cgactgaata cgtagcggaa                    40

<210> SEQ ID NO 19
<211> LENGTH: 39
<212> TYPE: DNA
<213> ORGANISM: Artificial Sequence
<220> FEATURE:
<221> NAME/KEY: misc_feature
<223> OTHER INFORMATION: Description of Artificial Sequence:synthetic
      DNA

<400> SEQUENCE: 19
atcttggatc cggttgtgtg atgttattca aggtttgcg                     39
```

US 6,331,428 B1

HEXULOSE PHOSPHATE ISOMERASE GENE

This application is a continuation-in-part of application Ser. No. 09/033,647 filed on Mar. 3, 1998, now abandoned.

TECHNICAL FIELD

The present invention relates to a DNA coding for hexulose phosphate isomerase, and a method for producing hexulose phosphate isomerase.

BACKGROUND ART

The ribulose monophosphate pathway is known for C1 metabolism of methylotroph bacteria. This pathway comprises three stages starting from fixation of formaldehyde with ribulose 5-phosphate, followed by cleavage of fructose 6-phosphate and regeneration of ribulose 5-phosphate. The ribulose monophosphate pathway is a pathway which is coupled to several metabolic systems. The gene structures of respective enzymes involved in this pathway have been of great interest. However, few reports have been submitted on this pathway, and little genetic analysis has been achieved.

3-Hexulose-6-phosphate synthase (hereinafter referred to as "HPS", if necessary), which catalyzes the initial reaction of the ribulose monophosphate pathway, has been already purified from *Methylomonas aminofaciens* which is a Gram-negative obligate methanol-assimilating bacterium. A gene coding for this enzyme has been cloned, and its primary structure has been reported (Yanase, H. et al., FEMS *Microbiol. Lett.*, 135, 201–205 (1996)).

By the way, the biochemical substance, in which a specific position on the objective compound molecule is labeled with a stable isotope element, i.e., carbon 13 ($^{13}C$), is useful for the study of metabolic pathway of the organism. Recently, the investigation of the situation of metabolic substances in vivo based on the use of the carbon 13-NMR is an extremely important technique for diagnosis of various diseases and daily health examination. It is necessary, or it has been demanded, for such a new technique, to inexpensively supply a substance in which a certain objective position is labeled with carbon 13.

The present inventor has been established a method for preparing [1-$^{13}C$]D-glucose 6-phosphate from carbon 13-labeled methanol by utilizing the formaldehyde-fixing pathway of a methanol-assimilating bacterium. However, the yield of synthesis of the objective compound has not been so high (*Biosci. Biotech. Biochem.*, 5, 308–312 (1993)).

Therefore, it has been demanded to obtain a system which makes it possible to efficiently produce only the objective product. A method is conceived as one of such systems, in which a series of respective enzymes for synthesizing labeled D-fructose 6-phosphate by using labeled formaldehyde and ribulose 5-phosphate are prepared, and a reaction system is constructed based on the use of the enzymes to efficiently prepare the objective labeled compound. As for HPS which is the initial enzyme in the reaction system, its gene has been isolated from *Methylomonas aminofaciens* as described above, and its structure has been also clarified. However, hexulose-phosphate isomerase (hereinafter referred to as "HPI" or phospho-3-hexuloisomerase (PHI), if necessary), which is an enzyme to catalyze the next step reaction, has been purified only partially, and neither its amino acid sequence nor gene structure has been known. Further, neither amino acid sequence nor gene structure has been reported for both enzymes of HPS and HPI of Gram-positive bacteria including the genus *Mycobacterium* as facultative methanol-assimilating bacteria.

In the circumstance as described above, in order to establish a system for efficiently preparing an objective labeled compound, it has been demanded to isolate a gene coding for HPI and provide a method for efficiently producing HPI based on the use of the gene.

DISCLOSURE OF THE INVENTION

The present invention has been made taking the foregoing viewpoints into consideration, an object of which is to provide a DNA coding for HPI and a method for utilizing the DNA.

The present inventor has been investigated the ribulose monophosphate pathway, especially HPS and its gene in *Mycobacterium gastri* which is a Gram-positive facultative methanol-assimilating bacterium. During this investigation, the present inventor has unexpectedly found a gene coding for HPI of this strain. Thus, the present invention has been completed.

That is, the present invention lies in a DNA coding for a protein as defined in the following (A) or (B):

(A) a protein which has an amino acid sequence depicted in SEQ ID NO: 13 in Sequence Listing; or (B) a protein which comprises an amino acid sequence including substitution, deletion, insertion, addition, or inversion of one or several amino acids in the amino acid sequence depicted in SEQ ID NO: 13 in Sequence Listing, and which has a hexulose phosphate isomerase activity.

Specifically, the DNA described above includes DNA as defined in the following (a) or (b):

(a) a DNA which contains a nucleotide sequence corresponding to at least nucleotide numbers of 608 to 1204 of a nucleotide sequence depicted in SEQ ID NO: 12 in Sequence Listing; or (b) a DNA which is hybridizable with the nucleotide sequence corresponding to at least nucleotide numbers of 608 to 1204 of the nucleotide sequence depicted in SEQ ID NO: 12 in Sequence Listing under a stringent condition, and which codes for the protein having the hexulose phosphate isomerase activity.

In another aspect, the present invention provides a cell into which the DNA is introduced in a form capable of expressing hexulose phosphate isomerase encoded by the DNA.

In still another aspect, the present invention provides a method for producing hexulose phosphate isomerase, comprising the steps of cultivating the cell in a medium to produce and accumulate the hexulose phosphate isomerase in a culture, and collecting the hexulose phosphate isomerase from the culture.

In the present invention, the term "hexulose phosphate isomerase activity" refers to an activity to catalyze an isomerization reaction between 3-hexulose 6-phosphate and fructose 6-phosphate.

The present invention will be explained in detail below.

<1>DNA of the Present Invention

The DNA of the present invention has been obtained from chromosomal DNA of *Mycobacterium gastri* as follows, as explained in Examples described later on.

At first, HPS is purified from *Mycobacterium gastri* MB19 strain. HPS can be purified from a cell-free extract solution of MB19 strain up to give a single band on SDS-PAGE by means of DEAE-sepharose column chromatography, phenylsepharose column chromatography, and DEAE-sepharose column chromatography. In each of the purification steps, the HPS activity can be measured in accordance with the method described in *Methods in Enzymology*, Vol. 188, 397–401 (1990).

Next, partial amino acid sequences of purified HPS are determined. Oligonucleotide primers to be used for PCR (polymerase chain reaction) are synthesized on the basis of the obtained amino acid sequence information to perform PCR by using a template of genomic DNA prepared from *Mycobacterium gastri* MB19 strain. The genomic DNA can be obtained in accordance with the method of Saito et al. (see *Biochim. Biophys. Acta*, 72, 619–629 (1963)). The cultivation to obtain bacterial cells used for preparing the genome is performed by using a medium containing methanol as a carbon source added with 1% of glycine. By doing so, a large amount of bacterial cells can be obtained, making it easy to perform the bacteriolysis operation. As for the bacteriolytic enzyme, sufficient bacteriolysis is not achieved, if only lysozyme is used. However, the use of N-acethylmuramidase SG is effective.

When oligonucleotides having nucleotide sequences shown in SEQ ID NO: 8 and SEQ ID NO: 9 in Sequence Listing are used as the primers, a DNA fragment of about 400 bp is obtained by means of PCR as described above.

Next, colony hybridization is performed for a library comprising PstI-digested fragments of the genomic DNA of *Mycobacterium gastri* MB19 strain by using, as a DNA probe, the DNA fragment amplified by PCR as described above so that a positive clone is obtained.

A nucleotide sequence has been determined for about 3 kb of a clone fragment having a length of about 4.1 kb obtained as described above. An obtained result is shown in SEQ ID NO: 12 in Sequence Listing. Three open reading frames (ORF) are present in this region. Amino acid sequences encoded by the respective ORF's are successively shown in SEQ ID NOS: 13 to 15 from the 5'-terminal side. Among them, the second ORF (ORF-2) is completely coincident with a partial amino acid sequence of HPS. Therefore, the second ORF has been demonstrated to be a gene coding for HPS (hereinafter referred to as "hps", if necessary). On the other hand, the first ORF (ORF-1) has been confirmed to be a gene coding for HPI (hereinafter referred to as "hpi", if necessary), i.e., the DNA of the present invention, by investigating the activity of a protein obtained by expressing this ORF.

As described above, the DNA of the present invention has been unexpectedly obtained in association with the purification of HPS and the isolation of has. However, the DNA of the present invention has been obtained on the basis of the idea that ORF-1 may code for HPI, by expressing ORF-1, and confirming the activity of the expressed product. The amino acid sequence encoded by ORF-1 has been searched over various known data bases. However, it was impossible to find any significant correlation with polypeptides, functions of which were well known.

*Mycobacterium gastri*, which was used to isolate the DNA of the present invention, is a Gram-positive facultative methanol-assimilating bacterium. *Methylomonas aminofaciens*, from which hps has been already isolated, is a Gram-negative obligate methanol-assimilating bacterium. The both are taxonomically completely different from each other.

The DNA of the present invention has been obtained as described above, and its nucleotide sequence and the amino acid sequence encoded thereby have been clarified by the present invention. Therefore, the DNA of the present invention can be obtained from a genomic DNA library of a bacterium belonging to the genus *Mycobacterium*, for example, *Mycobacterium gastri* MB19 strain, by means of hybridization by using, as a probe, an oligonucleotide prepared on the basis of the nucleotide sequence or the amino acid sequence. The DNA of the present invention can be also obtained by performing PCR by using the oligonucleotides as primers and using genomic DNA of a bacterium belonging to the genus *Mycobacterium* as a template.

The methods to perform, for example, preparation of the genomic DNA library, hybridization, PCR, preparation of plasmid DNA, digestion and ligation of DNA, and transformation are described by Sambrook, J., Fritsche, E. F., Maniatis, T. in *Molecular Cloning*, Cold Spring Harbor Laboratory Press, 1.21 (1989).

*Escherichia coli* JM109/pT-HPIS-1 obtained in Examples described later on, which contains the DNA of the present invention and which contains a plasmid pT-HPIS-1 capable of expressing HPI under the control of tryptophan operon promoter, has been awarded a private number of AJ13363, and deposited since Aug. 4, 1997 in National Institute of Bioscience and Human Technology of Agency of Industrial Science and Technology of Ministry of International Trade and Industry (zip code: 305-8566, 1–3 Higashi 1-Chome, Tsukuba-shi, Ibaraki-ken, Japan), as an accession number of FERM P-16363, and transferred from the original deposition to international deposition based on Budapest Treaty on Jan. 16, 1998, and has been deposited as an accession number of FERM BP-6225.

The DNA of the present invention may code for HPI including substitution, deletion, insertion, addition, or inversion of one or several amino acids at one or a plurality of positions, provided that the activity of HPI encoded thereby is not deteriorated. The number of "several" amino acids differs depending on the position or the type of amino acid residues in the three-dimensional structure of the protein. This is because of the following reason. That is, some amino acids such as isoleucine and valine are amino acids having high homology to one another. The difference in such an amino acid does not greatly affect the three-dimensional structure of the protein. Therefore, the protein encoded by the DNA of the present invention may be one which has homology of not less than 30 to 40%, preferably not less than 55 to 65% with respect to the entire amino acid sequence for constituting HPI, and which has the HPI activity. More appropriately, the number of "several" amino acids is 2 to 140, preferably 2 to 90, and more preferably 2 to 10.

DNA, which codes for the substantially same protein as HPI as described above, is obtained, for example, by modifying the nucleotide sequence, for example, by means of the site-directed mutagenesis method so that one or more amino acid residues at a specified site involve substitution, deletion, insertion, addition, or inversion. DNA modified as described above may be obtained by the conventionally known mutation treatment. The mutation treatment includes a method for treating DNA coding for HPI in vitro, for example, with hydroxylamine, and a method for treating a microorganism, for example, a bacterium belonging to the genus Escherichia harboring DNA coding for HPI with ultraviolet irradiation or a mutating agent such as N-methyl-N'-nitro-N-nitrosoguanidine (NTG) and nitrous acid usually used for the mutation treatment.

The substitution, deletion, insertion, addition, or inversion of nucleotide as described above also includes mutation (mutant or variant) which naturally occurs, for example, on the basis of the individual difference or the difference in species or genus of the microorganism which harbors hpi.

The DNA, which codes for substantially the same protein as HPI, is obtained by expressing DNA having mutation as described above in an appropriate cell, and investigating the HPI activity of an expressed product. The DNA, which codes for substantially the same protein as HPI, is also obtained by isolating DNA which is hybridizable with. DNA having, for example, a nucleotide sequence corresponding to nucleotide numbers of 608 to 1204 of the nucleotide sequence depicted in SEQ ID NO: 12 in Sequence Listing under a stringent condition, and which codes for a protein having the HPI activity, from DNA coding for HPI having mutation or from a cell harboring it. The "stringent condition" referred to herein is a condition under which so-called specific hybrid is formed, and non-specific hybrid is not formed. It is difficult to clearly express this condition by using any numerical value. However, for example, the stringent condition includes a condition under which DNA's having high homology, for example, DNA's having homology of not less than 50% are hybridized with each other, and DNA's having homology lower than the above are not hybridized with each other. Alternatively, the stringent condition is exemplified by a condition under which DNA's are hybridized with each other at a salt concentration corresponding to an ordinary condition of washing in Southern hybridization, i.e., 60° C., 1×SSC, 0.1% SDS, preferably 0.1×SSC, 0.1% SDS.

The gene, which is hybridizable under the condition as described above, includes those having a stop codon generated in the middle of the gene, and those having no activity due to mutation of active center. However, such inconveniences can be easily removed by ligating the gene with a commercially available activity expression vector, and measuring the HPI activity in accordance with the method described above.

<2> Production of Hexulose Phosphate Isomerase

HPI can be produced by expressing the DNA of the present invention described above by using an appropriate host-vector system.

The host to be used for expressing the hpi gene includes various prokaryotic cells represented by *Escherichia coli*, various eukaryotic cells represented by *Saccharomyces cerevisiae*, animal cells, and plant cells. Among them, it is preferable to use prokaryotic cells, especially *Escherichia coli*.

The vector to be used for introducing the hpi gene into the host as described above includes, for example, pUC19, pUC18, pBR322, pHSG299, pHSG298, pHSG399, pHSG398, RSF1010, pMW119, pMW118, pMW219, and pMW218. Besides, it is possible to utilize phage DNA vectors. The hpi gene can be introduced by transforming the host with a recombinant vector obtained by connecting the hpi gene to the vector as described above. The hpi gene may be incorporated into the genome of the host in accordance with the method based on the use of transduction, transposon (Berg, D. E. and Berg, C. M., *Bio/Technol.*, 1, 417 (1983)), Mu phage (Japanese Laid-Open Patent Publication No. 2-109985), or homologous recombination (*Experiments in Molecular Genetics*, Cold Spring Harbor Lab. (1972)).

In order to efficiently express the hpi gene, it is also preferable to connect a promoter such as lac, trp, and PL which functions in the host cell, at a position upstream from the DNA sequence coding for HPI. When a vector containing a promoter is used as the vector, it is possible to ligate the hpi gene with the vector or the promoter at once. Such a vector is exemplified by pT13 sNco containing trp promoter (see *J. Biochem.*, 104, 30–34 (1988)).

Transformation may be performed by using, for example, a method in which recipient cells are treated with calcium chloride to increase the permeability of DNA, as reported for *Escherichia coli* K-12 (Mandel, M. and Higa, A., *J. Mol. Biol.*, 53, 159 (1970)), or a method in which competent cells are prepared from cells at the proliferating stage to introduce DNA, as reported for *Bacillus subtilis* (Duncan, C. H., Wilson, G. A. and Young, F. E., *Gene*, 1, 153 (1977)). Alternatively, it is also possible to apply a method in which DNA recipient cells are allowed to be in a state of protoplasts or spheroplasts capable of incorporating recombinant DNA with ease to introduce recombinant DNA into the DNA recipient cells, as known for *Bacillus subtilis*, actinomycetes, and yeasts (Chang, S. and Choen, S. N., *Molec. Gen. Genet.*, 168, 111 (1979); Bibb, M. J., Ward, J. M. and Hopwood, O. A., *Nature*, 274, 398 (1978); Hinnen, A., Hicks, J. B. and Fink, G. R., *Proc. Natl. Acad. Sci. USA*, 75, 1929 (1978)). These methods may be appropriately selected depending on the cell to be used as the host.

The hpi gene includes all that provide the HPI activity upon expression. Preferably, the hpi gene includes genes containing DNA coding for an amino acid sequence depicted in SEQ ID NO: 13 in Sequence Listing, or DNA comprising a nucleotide sequence represented by nucleotide numbers of 608 to 1204 of the nucleotide sequence depicted in SEQ ID NO: 12 in Sequence Listing. The hpi gene may be those which contain DNA coding for HPI including substitution, deletion, insertion, addition, or inversion of one or several amino acids at one or a plurality of positions, provided that the activity of encoded HPI is not deteriorated.

HPI can be produced by cultivating the cells introduced with the hpi gene as described above in a medium to produce and accumulate HPI in a culture, and collecting HPI from the culture. The medium to be used for the cultivation may be appropriately selected depending on the host to be used. It is preferable to use M9-casamino acid-glucose medium when *Escherichia coli* is used as the host, and hpi is expressed by using the trp promoter. Cultivation is performed at 37° C. Several hours after the start of the cultivation, indole acrylic acid (IAA) as an inducing agent for the trp promoter is added so that the final concentration is 25 $\mu$g/ml, and the cultivation is further continued. Thus, HPI is accumulated in the bacterial cells. Alternatively, when HPI is produced and secreted to the outside of cells by using an appropriate secretion system, HPI is accumulated in a medium.

HPI produced as described above can be purified, if necessary, from a cell-free extract solution or a medium by using an ordinary enzyme purification method such as ion exchange chromatography, gel filtration chromatography, adsorption chromatography, and solvent precipitation.

HPI obtained according to the present invention can be utilized to prepare [1-$^{13}$C]D-glucose 6-phosphate from carbon 13-labeled methanol. [1-$^{13}$C]D-glucose 6-phosphate can be prepared, for example, as follows. Methanol is oxidized into formaldehyde by using alcohol oxidase prepared from a methanol-assimilating yeast, *Candida boydinie*. Obtained formaldehyde is subjected to aldol condensation with ribulose 5-phosphate in accordance with the action of HPS to produce arabino-3-hexulose 6-phosphate. In this process, since ribulose 5-phosphate is unstable, ribose 5-phosphate is isomerized into ribulose 5-phosphate in the same reaction system in accordance with the action of phosphoriboisomerase, to be used for the HPS reaction. Arabino-3-hexulose 6-phosphate, which is produced by the foregoing reaction, is converted into fructose 6-phosphate in accordance with the action of HPI. Then, fructose 6-phosphate produced by HPI is converted into glucose 6-phosphate with the action of glucose 6-phosphate isomerase. In general, the HPI content of the methanol-assimilating bacteria is remarkably low as compared with HPS. For this reason, it has been difficult to utilize HPI for the foregoing reaction. However, hpi has been isolated, and the method for efficiently producing HPI has been provided according to the present invention. Therefore, it becomes possible to practically use the foregoing reaction.

According to the method of the present invention, the DNA coding for hexulose phosphate isomerase is obtained, and it is possible to efficiently produce the enzyme. Consequently, it is possible to inexpensively provide a large amount of the labeled compound which is important and necessary for the medical treatment and the biochemical fundamental study.

BEST MODE FOR CARRYING OUT THE INVENTION

The present invention will be explained in further detail below with reference to Examples.

EXAMPLE 1

Cloning of hpi Gene of *Mycobacterium gastri*

MB19 Strain and Expression of HPI

<1> Purification of 3-hexulose-6-phosphate Synthase

*Mycobacterium gastri* MB19 strain was cultivated at 30° C. for 24 hours with a jar fermentor of 10 liters (L) by using a basic medium containing methanol as a sole carbon source [composition: 1% (v/v) methanol, 0.2% $NaNO_3$, 0.2% $(NH_4)_2SO_4$, 0.2% $K_2HPO_4$, 0.1% $KH_2PO_4$, 0.02% $MgSO_4.7H_2O$, 0.02% yeast extract, 0.2% (v/v) vitamin solution (obtained by dissolving 40 mg calcium pantothenate, 20 mg inositol, 40 mg nicotinic acid, 20 mg p-aminobenzoic acid, 40 mg pyridoxine hydrochloride, 0.2 mg biotin, and 40 mg thiamine hydrochloride in 100 ml of distilled water), and 1% (v/v) trace metal salt solution (obtained by dissolving 0.2 g $CaCl_2.2H_2O$, 0.2 g $MnSO_4.7H_2O$, 0.2 g $ZnSO_4.7H_2O$, 0.02 g $CuSO_4.5H_2O$, 0.1 g $FeSO_4.7H_2O$, 0.05 g $Na_2MoO_4.2H_2O$, 0.25 g $H_3BO_4$, and 0.05 KI in 100 ml of distilled water)]. Bacterial cells were collected (by means of continuous centrifugation at 6,500× g) from 10 L of the culture fluid to obtain 80 g of wet bacterial cells.

The obtained bacterial cells were suspended to give a concentration of 10% (w/v) in Buffer A (10 mM Tris-HCl (pH 8.2), 1 mM dithiothreitol, 5 mM magnesium chloride, and 0.15 mM phenylmethylsulfonylfluoride). Subsequently, the bacterial cells in the suspension were disrupted with ultrasonic at an intensity of 180 W, followed by ultracentrifugation at 120,000×g for 60 minutes. After that, a supernatant fraction thereof was obtained as a cell-free extract solution. The cell-free extract solution was subjected to DEAE-sepharose ion exchange column chromatography equilibrated with Buffer A. Under this condition, the objective HPS protein was adsorbed to the column. The objective HPS protein was eluted from the column by applying a concentration gradient of buffering agent by using a buffer containing Tris-HCl at a high concentration (100 mM Tris-HCl (pH 8.2), 1 mM dithiothreitol, 5 mM magnesium chloride, and 0.15 mM phenylmethylsulfonylfluoride), and enzyme activity fractions were recovered. As a result, it was possible to obtain an HPS sample which was purified about 19-fold.

Next, the HPS sample was dialyzed against 10 mM potassium phosphate buffer (pH 7.0) (Buffer B) containing 3 M NaCl, 1 mM dithiothreitol, 5 mM magnesium chloride, and 0.15 mM phenylmethylsulfonylfluoride. The dialyzed sample was subjected to hydrophobic chromatography by using a phenylsepharose column equilibrated with the same buffer. Under this condition, HPS was adsorbed to the column. Subsequently, the protein was eluted by applying a concentration gradient to the column by using a buffer containing ethylene glycol (50% ethylene glycol, 1 mM dithiothreitol, 5 mM magnesium chloride, 0.15 mM phenylmethylsulfonylfluoride, and 10 mM potassium phosphate buffer (pH 7.0)), and fractions exhibiting the HPS activity were collected. At this stage, HPS was successfully purified 31-fold.

In order to further increase the purity of the sample, the sample was subjected to the DEAE-sepharose column again under the same equilibration and elution conditions as those described above. Thus, HPS was successfully purified at a yield of 47% with a specific activity of 42-fold to give a single band on SDS-PAGE.

Basically, in each of the purification steps, the HPS activity was measured in accordance with the method described in *Methods in Enzymology*, Vol. 188, 397–401 (1990). Specifically, the method was carried out as follows. Into an enzyme reaction cuvette were introduced 0.5 M potassium phosphate buffer (pH 7.5) 0.05 ml, 50 mM magnesium chloride 0.05 ml, 50 mM ribose 5-phosphate 0.05 ml, 100 U/ml phosphoriboisomerase (produced by Sigma) 0.05 ml, and water 0.15 ml. The sample for activity measurement was added in an amount of 0.05 ml to the cuvette, followed by mixing. The reaction mixture was preincubated at 30° C. for 2 minutes, to which 10 mM formaldehyde was added in an amount of 0.1 ml to start the enzyme reaction. After performing the reaction at 30° C. for 5 minutes, 0.1 ml of 0.5 M HCl was added to the reaction solution to stop the reaction. The reaction solution was diluted 20-fold, to which 2 ml of Nash reagent was added (see *Biochem. J.*, 5, 416 (1953)) to measure the degree of decrease of formaldehyde in the solution. A reaction system, which was obtained by adding water in place of ribose 5-phosphate, was used for a control experiment.

<2> Cloning of hps Gene

Purified HPS obtained as described above was applied to a protein sequencer to determine 30 residues of N-terminal sequence (MKLQVAIDLLSTEAALELAGKVAEYVDIIE (SEQ ID NO: 1)). Purified HPS was treated with lysyl endopeptidase to obtain degraded peptide fragment products which were fractionated by using reversed-phase HPLC. Obtained fractions were analyzed by using the protein sequencer respectively. Thus, internal amino acid sequences of HPS were determined (VAEYVDIIELGTPLIK (SEQ ID NO: 2), IVFADMK (SEQ ID NO: 3), ATRAQEVRALGAK (SEQ ID NO: 4), FVEMHAGLDEQAK (SEQ ID NO: 5), ARVPFSVAGGVK (SEQ ID NO: 6), VATIPAVQK (SEQ ID NO: 7)).

In order to amplify the hps gene by means of PCR on the basis of the amino acid sequence information as described above, an oligonucleotide having a nucleotide sequence (5'-ATGAARYTICARGTNGCIATHGA-3') depicted in SEQ ID NO: 8 was chemically synthesized as an N-terminal primer, and an oligonucleotide having a nucleotide sequence (5'-CCNGCRTGCATYTCNACRAA-3') depicted in SEQ ID NO: 9 was chemically synthesized as an internal primer. These primers were used to perform PCR by using a template of genomic DNA prepared from *Mycobacterium gastri* MB19 strain to obtain a DNA fragment of about 400 bp. The genomic DNA used as the template was obtained with reference to the method of Saito et al. (see *Biochim. Biophys. Acta*, 72, 619–629 (1963)). Cultivation was performed by using the basic medium containing ethanol as a carbon source to make it possible to obtain a large amount of bacterial cells. However, it was revealed that the bacteriolysis operation was difficult if the medium was used as it was. Accordingly, the culture fluid was added with 1% glycine. Further, if only lysozyme was used, sufficient bacteriolysis was not achieved. For this reason, various solubilizing enzymes were investigated. As a result, N-acethylmuramidase SG was effective, which was used. The PCR was performed with repeating a reaction 25 times, condition of which was at 95° C. for one minute, at 55° C. for one minute and at 72° C. for one minute, using Ex Taq-DNA polymerase produced by Takara Shuzo Co.,Ltd. The DNA fragment thus obtained as described above was used in turn as a DNA probe to perform genomic Southern analysis for genomic DNA of *Mycobacterium gastri* MB19 strain having been treated with various restriction enzymes. As a result, it was revealed that the probe hybridized with a DNA fragment having a size of about 4.1 kb excised by treating the genomic DNA with PstI. On the basis of this result, genomic DNA fragments of *Mycobacterium gastri* MB19 strain digested with PstI were ligated with pUC118 as a vector to prepare a genome library which was subjected to colony hybridization by using the DNA probe described above to obtain a positive clone. A plasmid of about 7.2 kbp was obtained from this clone. This plasmid was designated as pUHM1.

<3> Determination of Nucleotide Sequence of hps Gene

Next, a nucleotide sequence of DNA of about 3 kb of the inserted DNA fragment on the plasmid pUHM1 was determined. An obtained result is shown in SEQ ID NO: 12 in Sequence Listing. As a result, three open reading frames (ORF) were present in this region. Amino acid sequences encoded by the respective ORF's are successively shown in SEQ ID NO: 13 to SEQ ID NO: 15 from the 5'-terminal side.

The second ORF (ORF-2) coded for a protein composed of 207 amino acid residues having a molecular weight of 21,000 determined therefrom. This value was approximately coincident with a molecular weight of 24,000 determined from the subunit of purified HPS. An amino acid sequence (SEQ ID NO: 14) encoded by ORF-2 completely corresponded to the seven amino acid sequences (the N-terminal amino acid sequence and the internal amino acid sequences) obtained from the purified protein. Accordingly, it has been demonstrated that ORF-2 is the gene (hps) coding for HPS.

On the other hand, the amino acid sequence of ORF (ORF-1) upstream from hps was searched for various known data bases by using the program of Blast (Basic Local Alignment Search Tool). As a result, it was impossible to find any significant correlation with polypeptides, functions of which were well known.

<4> Expression of ORF-1

ORF-1 existing upstream from hps obtained as described above was forcedly expressed to try to investigate the activity of the protein encoded thereby. Two oligonucleotides, i.e., 5'-CGAAATCGATAAAAATGACGCAAGCCGCAGA AGCCGACGGCG-3' (SEQ ID NO: 10) and 5'-AATTCCAGCTCTAGACAAGGCGGTACGGCG-3' (SEQ ID NO: 11) were synthesized. PCR was performed by using the synthesized oligonucleotides as primers and using the plasmid pUHM1 as a template to prepare a DNA fragment (A) containing ORF-1 and having a ClaI site at its upstream end and an XbaI site at its downstream end.

On the other hand, pT13 sNco (see *J. Biochem.*, 104, 30–34 (1988)) having tryptophan promoter was used as a high level expression plasmid for expressing the DNA fragment (A). pT13sNco was digested with restriction enzymes ClaI and XbaI to prepare an obtained large DNA fragment (B). The DNA fragment (A) was ligated with the DNA fragment (B) by using T4 DNA ligase to construct an expression plasmid for ORF-1, i.e., pT-HPIS-1.

pT-HPIS-1 was used to transform *Escherichia coli* JM109 strain in accordance with an ordinary method to obtain a transformant JM109/pT-HPIS-1. On the other hand, *Escherichia coli* JM109 strain (JM109/pTTNco) harboring pTTNco as a vector portion of pT13sNco was used as a control strain transformed with a plasmid not containing the DNA fragment (A).

Each of the transformants was cultivated with shaking at 37° C. in the M9-casamino acid-glucose medium. After about 2 hours, the medium was added with indole acrylic acid (IAA) as an inducing agent for transcription from the tryptophan promoter to give a final concentration of 25 μg/ml, followed by continuing cultivation for further 4 hours. After that, 1.5 ml of the culture fluid was collected. Obtained bacterial cells were added with 0.5 ml of 0.1 M potassium phosphate buffer (pH 7.5), followed by being suspended. Subsequently, the bacterial cells were disrupted by ultrasonic, followed by centrifugation (15,000 rpm×5 minutes) to obtain a soluble fraction to be used as an enzyme sample.

The HPI activity was measured for the enzyme sample. The activity was measured in accordance with a method in which assimilation of formaldehyde was finally measured on the basis of reduction of oxidized nicotinamide adenine dinucleotide phosphate effected by glucose-6-phosphate dehydrogenase.

Specifically, a reaction solution [20 mM potassium phosphate (pH 7.5), 1 mM magnesium chloride, 1 mM ribose 5-phosphate, 0.8 mM $NADP^+$ (oxidized nicotinamide adenine dinucleotide phosphate), 3 U/ml phosphoriboisomerase (produced by Sigma), 3.5 U/ml phosphoglucoisomerase (produced by Boehringer), 3.5 U/ml glucose-6-phosphate dehydrogenase (produced by Boehringer), and 3 U/ml HPS] was introduced in an amount of 0.9 ml into a cuvette for a spectrophotometer (for the sample or for the control). After that, the soluble fraction obtained from the bacterial cells was added in an amount of 0.05 ml to each cuvette, followed by being mixed. After maintaining the temperature at 30° C. for 2 minutes, the reaction was started by adding 0.05 ml of water to the control cuvette, or by adding 0.05 ml of 0.1 M formaldehyde to the sample cuvette. The HPI activity was measured by using an index of the increase in absorbance of light at a wavelength of 340 nm associated with the reduction of $NADP^+$. HPS used in the activity measurement was prepared as follows. That is, an hps gene originating from *Methylomonas aminofaciens* 77a strain was incorporated into *Escherichia coli* in accordance with a known method described in FEMS microbiology letter, 135, 201–205 (1996) to obtain a strain which was used to mass-produce HPS which was purified in accordance with a known method described in *Argic. Biol. Chem.*, 41, 1133–1140 (1997).

As a result, when the cell extract solution obtained from the control strain (JM109/pTTNco) was used, the HPI enzyme activity was not exhibited at all. However, when the extract solution of JM109/pTHPIS-1 was used, the distinct HPI enzyme activity was successfully detected unexpectedly. According to this fact, it has been revealed that ORF-1 is the gene coding for HPI.

The amino acids of the encoded HPI were compared between the hpi gene of *Mycobacterium gastri* MB19 strain obtained as described above and the hpi gene cloned from

*Methylomonas aminofaciens* 77a strain in the same manner as described above. As a result, the homology was found for the first time. The homology concerning completely the same amino acids was about 30%, and the homology concerning completely the same amino acids as well as similar amino acids was about 69%.

EXAMPLE 2

Identification of hpi Gene of *Bacillus subtilis* 168 strain

<1> Data Base Searching of HPI Amino Acid Sequence

For the amino acid sequence of HPI of *Mycobacterium gastri* MB19 strain obtained by the same manner as Example 1, homology search was performed for known data bases including ORF function of which was unknown. This search was carried out using SWISS-PROT Rel.34 with searching system of Genetyx-Mac (Softwear Development). As a result, yckF (SEQ ID NO: 16) of *Bacillus subtilis* 168 strain, function of which was unknown, was found as the sequence having high homology with the amino acid sequence encoded by hpi gene of *Mycobacterium gastri* MB19 strain.

As a result of comparing the amino acid sequence of HPI of *Mycobacterium gastri* MB19 strain with the amino acid sequence (SEQ ID NO: 17) encoded by yckF of *Bacillus subtilis* 168 strain, the homology concerning completely the same amino acids was about 35%, and the homology concerning completely the same amino acids as well as similar amino acids was about 76%. It was unexpected that there was the gene coding for a protein having high homology with HPI in *Bacillus subtilis* which was not naturally concerned with assimilation of C1 compound such as methanol. Then, in order to determine whether this yckF had the HPI activity, the yckF gene was isolated from *Bacillus subtilis* and incorporated into an expression vector. Then the obtained recombinant vector was introduced into the cells of *Escherichia coli* and the HPI activity in the cell crude extract solution was measured.

<2> Cloning of yckF Gene of *Bacillus Subtilis*

As a whole genomic nucleotide sequence of *Bacillus subtilis* was already determined (*Nature, Vol.*390, pp249, 1997), a DNA fragment including yckF was amplified by means of PCR on the basis of the nucleotide sequence information. Used DNA primers in PCR were an oligonucleotide having a nucleotide sequence (5'AAGCATCGATAAAATGAAAACGACTGAATACG TAGCGGAA3') depicted in SEQ ID NO: 18 as a primer which has a ClaI site upstream on the N-terminal side, and an oligonucleotide having a nucleotide sequence (5'ATCTTGGATCCGGTTGTGTGATGTTATTCAAG TTTGCG3') depicted in SEQ ID NO: 19 as a primer which has a BamHI site downstream on the C-terminal side. These primers were used to perform PCR by using a template of genomic DNA prepared from *Bacillus subtilis* 168 strain to obtain an amplified DNA fragment of about 550 bp. The genomic DNA used as the template was obtained according to the method of Saito et al. (see *Biochim. Biophys. Acta*, 72, 619–629 (1963)). The PCR was performed with heat-treating at 94° C. for 90 seconds, repeating a reaction 28 times, condition of which was at 98° C. for 10 seconds, at 58° C. for 20 seconds, and at 70° C. for 60 seconds, and reacting at 70° C. for 3 minutes, in above order, using LA-Taq enzyme produced by Takara Shuzo Co.,Ltd.

After the DNA fragment obtained as described above was purified by phenol treatment, alcohol precipitation, and the like, it was dissolved in an appropriate buffer solution for enzyme reaction. Subsequently, restriction enzymes ClaI and BamHI were added thereto, and the obtained solution was treated at 37° C. for one hour. Then, this reaction solution was applied to the gel electrophoresis of 0.8% agarose, to separate a DNA fragment, both ends of which were ClaI and BamHI digested ends, respectively. After that an objective DNA fragment was purified from this agarose gel to obtain a DNA fragment including yckf.

<3> Expression of yckF Gene of *Bacillus subtilis* and Confirmation of Enzyme Activity pT13 sNco having tryptophan promoter was used as a high level expression plasmid for expressing the yckF gene obtained as described above as well as Example 1. pT13sNco was digested with restriction enzymes ClaI and BamHI to prepare an obtained large DNA fragment. The DNA fragment including yckF as described above was ligated therewith by using T4 DNA ligase to construct an expression plasmid for yckF, i.e., pT-Bsb-yckF1.

pT-Bsb-yckF1 was used to transform *Escherichia coli* JM109 strain in accordance with an ordinary method to obtain a transformant JM109/pT-Bsb-yckF1. JM109/pT-Bsb-yckF1 has been awarded a private number of AJ13441, and deposited as international deposition based on Budapest Treaty since May 8, 1998 in National Institute of Bioscience and Human Technology of Agency of Industrial Science and Technology of Ministry of International Trade and Industry (zip code: 305-8566, 1–3 Higashi 1-Chome, Tsukuba-shi, Ibaraki-ken, Japan), as an accession number of FERM BP-6345.

On the other hand, *Escherichia coli* JM109 strain (JM109/pTTNco) harboring pTTNco as a vector portion of pT13sNco was used as a control strain transformed with a plasmid not containing the DNA fragment including yckf.

Each of the transformants was cultivated with shaking at 37° C. in the M9-casamino acid-glucose medium. After about 2 hours, the medium was added with indole acrylic acid as an inducing agent for transcription from the tryptophan promoter to give a final concentration of 25 μg/ml, followed by continuing cultivation for further 8 hours. After that, the culture fluid was collected and a soluble fraction from the bacterial cells was prepared by the same manner as in Example 1. Then, the HPI activity was measured.

As a result, when the cell extract solution obtained from the control strain (JM109/pTTNco) was used, the HPI enzyme activity was not exhibited at all. However, when the extract solution of JM109/pTBsb-yckF1 was used, the distinct HPI enzyme activity was detected. According to this fact, it was made known first that yckF (SEQ ID NO: 16) i.e. ORF function of which was unknown in *Bacillus subtilis* 168 strain was the gene coding for HPI. Further, since it is impossible for *Bacillus subtilis* to assimilate C1 compound such as methanol, it was not thought that *Bacillus subtilis* had the hpi gene. However, it was obvious that *Bacillus subtilis* had the hpi gene.

What is claimed is:

1. An isolated DNA coding for a protein which comprises the amino acid sequence of SEQ ID NO: 13, wherein
   (a) the DNA comprises the nucleotide sequence of bases 608 to 1204 of SEQ ID NO: 12; or
   (b) the DNA is hybridizable with the nucleotide sequence of bases 608 to 1204 of SEQ ID NO: 12 under a condition in which washing is performed at 60° C., and at a salt concentration corresponding to 1×SSC and 0.1% SDS, and wherein the DNA codes for a protein having hexulose phosphate isomerase activity,
   with the proviso that the DNA does not comprise the nucleotide sequence of SEQ ID NO: 16.

2. The DNA of claim 1, consisting of the DNA defined in (a).

3. The DNA of claim 1, consisting of the DNA defined in (b).

4. An isolated DNA coding for a protein which comprises the amino acid sequence of SEQ ID NO: 13.

5. A cell into which the DNA as defined in claim 1 is introduced in a form capable of expressing hexulose phosphate isomerase encoded by the DNA.

6. The cell according to claim 5, which is a microbial cell.

7. A cell into which the DNA as defined in claim 4 is introduced in a form capable of expressing hexulose phosphate isomerase encoded by the DNA.

8. The cell according to claim 7, which is a microbial cell.

9. A cell into which the DNA as defined in claim 2 is introduced in a form capable of expressing hexulose phosphate isomerase encoded by the DNA.

10. The cell according to claim 9, which is a microbial cell.

11. A cell into which the DNA as defined in claim 3 introduced in a form capable of expressing hexulose phosphate isomerase encoded by the DNA.

12. The cell according to claim 11, which is a microbial cell.

13. A method for producing hexulose phosphate isomerase, comprising cultivating the cell as defined in claim 5 in a medium, to produce and accumulate the hexulose phosphate isomerase, and collecting the hexulose phosphate isomerase.

14. A method for producing hexulose phosphate isomerase, comprising cultivating the cell as defined in claim 6 in a medium, to produce and accumulate the hexulose phosphate isomerase, and collecting the hexulose phosphate isomerase.

15. A method for producing hexulose phosphate isomerase, comprising cultivating the cell as defined in claim 7 in a medium, to produce and accumulate the hexulose phosphate isomerase, and collecting the hexulose phosphate isomerase.

16. A method for producing hexulose phosphate isomerase, comprising cultivating the cell as defined in claim 8 in a medium, to produce and accumulate the hexulose phosphate isomerase, and collecting the hexulose phosphate isomerase.

17. A method for producing hexulose phosphate isomerase, comprising cultivating the cell as defined in claim 9 in a medium, to produce and accumulate the hexulose phosphate isomerase, and collecting the hexulose phosphate isomerase.

18. A method for producing hexulose phosphate isomerase, comprising cultivating the cell as defined in claim 10 in a medium, to produce and accumulate the hexulose phosphate isomerase, and collecting the hexulose phosphate isomerase.

19. A method for producing hexulose phosphate isomerase, comprising cultivating the cell as defined in claim 11 in a medium, to produce and accumulate the hexulose phosphate isomerase, and collecting the hexulose phosphate isomerase.

20. A method for producing hexulose phosphate isomerase, comprising cultivating the cell as defined in claim 12 in a medium, to produce and accumulate the hexulose phosphate isomerase, and collecting the hexulose phosphate isomerase.

* * * * *

UNITED STATES PATENT AND TRADEMARK OFFICE
CERTIFICATE OF CORRECTION

| | |
|---|---|
| PATENT NO. | : 6,331,428 B1 |
| DATED | : December 18, 2001 |
| INVENTOR(S) | : Kato |

It is certified that error appears in the above-identified patent and that said Letters Patent is hereby corrected as shown below:

<u>Title page,</u>
Item [30], the Foreign Application Priority Data is listed incorrectly. Item [30] should read as follows:

-- [30]    Foreign Application Priority Data

Aug. 28, 1997   (JP)   ..............................   9-233131
    Jul. 9, 1998   (JP)   ..............................   10-194808 --

Signed and Sealed this

Nineteenth Day of March, 2002

Attest:

*Attesting Officer*

JAMES E. ROGAN
*Director of the United States Patent and Trademark Office*